(12) United States Patent
Savage

(10) Patent No.: US 6,699,211 B2
(45) Date of Patent: Mar. 2, 2004

(54) METHOD AND APPARATUS FOR TREATMENT OF GLAUCOMA

(76) Inventor: James A. Savage, 2058 Shell Ring Cir., Mt. Pleasant, SC (US) 29466

(*) Notice: Subject to any disclaimer, the term of this patent is extended or adjusted under 35 U.S.C. 154(b) by 192 days.

(21) Appl. No.: 09/934,357

(22) Filed: Aug. 21, 2001

(65) Prior Publication Data

US 2002/0026200 A1 Feb. 28, 2002

Related U.S. Application Data

(60) Provisional application No. 60/282,639, filed on Apr. 9, 2001, and provisional application No. 60/227,115, filed on Aug. 22, 2000.

(51) Int. Cl.$^7$ .......................... A61M 5/00; A61M 1/00; A61B 3/16; A61F 11/00
(52) U.S. Cl. ............................... 604/9; 604/8; 604/28; 604/30; 600/399; 606/108
(58) Field of Search ............................ 604/8, 9, 19, 27, 604/28, 30–31, 35, 500, 503, 505, 541, 65–67, 131, 264, 523, 284; 623/11.11, 23.64, 23.71, 24, 25, 26, 905, 907; 600/398–99, 561; 606/107, 108

(56) References Cited

U.S. PATENT DOCUMENTS

| | | | |
|---|---|---|---|
| 4,554,918 A | | 11/1985 | White |
| 5,433,701 A | | 7/1995 | Rubinstein |
| 5,626,558 A | | 5/1997 | Suson |
| 6,050,970 A | * | 4/2000 | Baerveldt .................... 604/28 |
| 6,168,575 B1 | * | 1/2001 | Soltanpour .................... 604/9 |

FOREIGN PATENT DOCUMENTS

| | | |
|---|---|---|
| AT | 409 586 B | 9/2002 |
| WO | WO 94/02081 | 2/1994 |
| WO | WO 01/78656 A2 | 10/2001 |
| WO | WO 01/97727 A1 | 12/2001 |

OTHER PUBLICATIONS

"Shunt Device and Method for Treating Glaucoma" Int'l. Appln. No. PCT/US00/11298; Int'l. Filing Date Apr. 26, 2000; Priority Date Apr. 26, 1999; Int'l. Pub. No. WO 00/64393; Int'l. Pub. Date Nov. 2, 2000; Applicants and Inventors: Mary G. Lynch, Reay H. Brown.

"Stent Device and Method for Treating Glaucoma" Int'l. Appln. No. PCT/US00/11215; Int'l. Filing Date Apr. 26, 2000; Priority Date Apr. 26, 1999; Int'l. Pub. No. WO 00/64391; Int'l. Pub. Date Nov. 2, 2000; Applicants and Inventors: Mary G. Lynch, Reay H. Brown.

"Long–Term Results with the White Glaucoma Pump––Shunt" vol. 21, No. 4, Apr. 1990, pp. 288–293 authored by Florence Davidovski, M.D.; Robert H. Stewart, M.D.; and Richard L. Kimbrough, M.D.

* cited by examiner

*Primary Examiner*—Patricia Bianco
(74) *Attorney, Agent, or Firm*—Brouse McDowell; Roger D. Emerson; Daniel A. Thomson

(57) ABSTRACT

A new and improved method and apparatus for treating glaucoma is described herein. A device for directing aqueous humor from an anterior chamber to Schlemm's canal comprises a seton, and may further comprise a pump operatively connected to the seton. The seton conducts aqueous directly from the anterior chamber to Schlemm's canal so that it can drain directly into the aqueous veins leading to the venous circulation. The seton for lowering intraocular pressure of an associated eye comprises a first tube adapted to be inserted into an associated anterior chamber of the eye; and, two wing tubes extending from the first tube. The two wing tubes are adapted to be inserted into Schlemm's canal. The two wing tubes and the first tube form a substantially continuous passageway, such that aqueous humor flows from the anterior chamber into Schlemm's canal through the substantially continuous passageway.

43 Claims, 9 Drawing Sheets

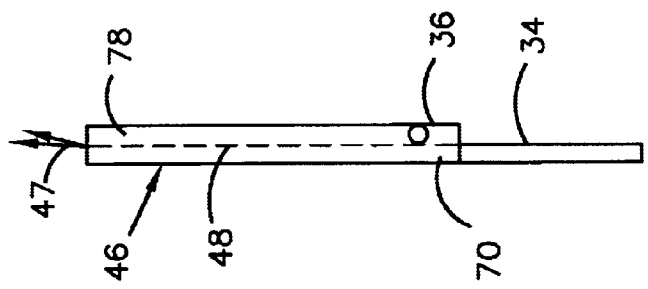
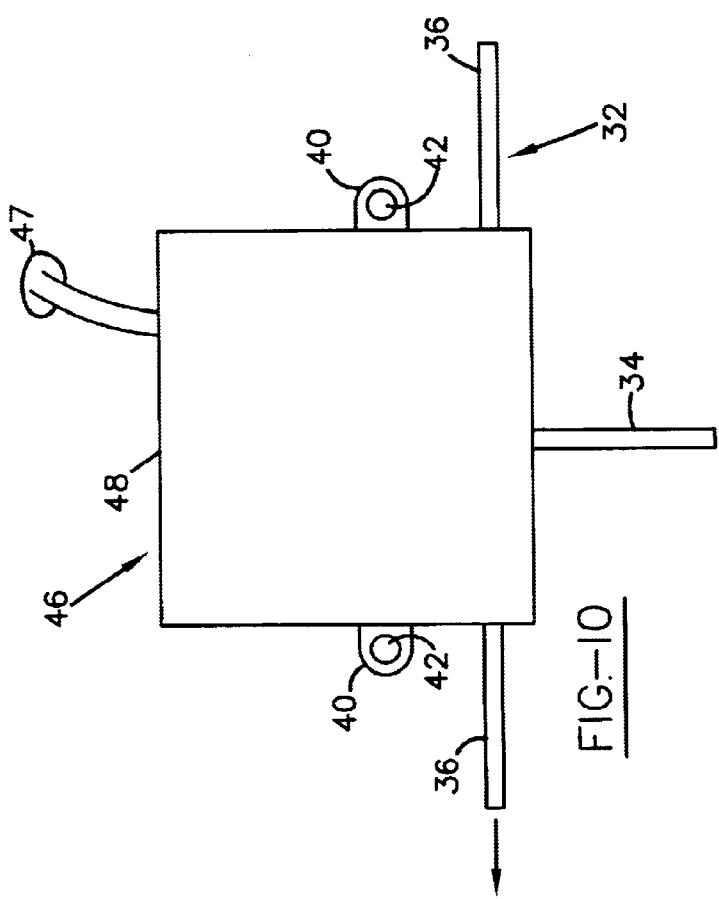
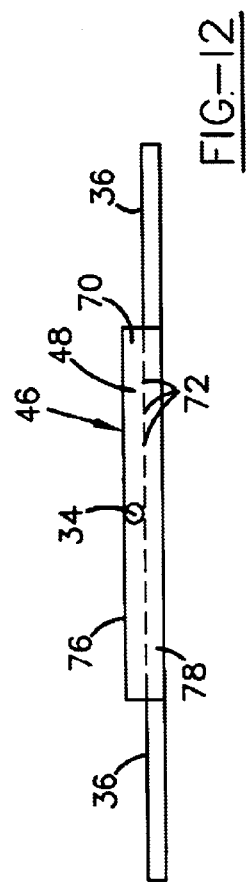

METHOD AND APPARATUS FOR TREATMENT OF GLAUCOMA

This application claims priority from a Provisional Application having Ser. No. 60/282,639, filed on Apr. 9, 2001, and from a Provisional Application having Ser. No. 60/227,115, filed on Aug. 22, 2000.

I. BACKGROUND OF THE INVENTION

A. Field of Invention

This invention relates to apparatuses and methods for treating glaucoma.

B. Description of the Related Art

It is known in the art that the treatment of glaucoma consists in lowering the intraocular pressure to a level that is tolerable for the optic nerve so that the progression of damage and visual loss is halted.

Glaucoma is a significant public health problem, because glaucoma is a major cause of blindness. The blindness that results from glaucoma involves both central and peripheral vision and has a major impact on an individual's ability to lead an independent life.

Glaucoma is an optic neuropathy (a disorder of the optic nerve) that usually occurs in the setting of an elevated intraocular pressure. The pressure within the eye increases and this is associated with changes in the appearance ("cupping") and function ("blind spots" in the visual field) of the optic nerve. If the pressure remains high enough for a long enough period of time, total vision loss occurs. High pressure develops in an eye because of an internal fluid imbalance.

The eye is a hollow structure that contains a clear fluid called "aqueous humor." Aqueous humor is formed in the posterior chamber of the eye by the ciliary body at a rate of approximately 2.5 microliters per minute. The fluid, which is made at a fairly constant rate, then passes around the lens, through the pupillary opening in the iris and into the anterior chamber of the eye. Once in the anterior chamber, the fluid drains out of the eye through two different routes. In the "uveoscleral" route, the fluid percolates between the muscle fibers of the ciliary body. This route accounts for approximately ten percent of the aqueous outflow in humans. The primary pathway for aqueous outflow in humans in through the "canalicular" route that involves the trabecular meshwork and Schlemm's canal.

The trabecular meshwork and Schlemm's canal are located at the junction between the iris and the sclera. This junction or corner is called "the angle." The trabecular meshwork is a ring of tissue, which is wedge-shaped in cross-section, that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal is adjacent to the trabecular meshwork. The outer wall of the trabecular meshwork coincides with the inner wall of Schlemm's canal. Schlemm's canal is a tube-like structure that runs around the circumference of the cornea.

The aqueous fluid travels through the spaces between the trabecular beams, across the inner wall of Schlemm's canal into the canal, through a series of about twenty-five collecting channels that drain from Schlemm's canal and into the episcleral venous system. In a normal situation, aqueous production is equal to aqueous outflow and intraocular pressure remains fairly constant in the 15 to 21 mmHg range. In most cases of glaucoma, the resistance through the canalicular outflow system is abnormally high.

In primary open angle glaucoma, which is the most common form of glaucoma, the abnormal resistance is believed to be along the outer aspect of the trabecular meshwork and the inner wall of Schlemm's canal. It is believed that an abnormal metabolism of the trabecular cells leads to an excessive buildup of extracellular materials or a buildup of abnormally "stiff" materials in this area. Histopathology of glaucoma eyes also demonstrates a collapse of Schlemm's canal. Primary open angle glaucoma accounts for approximately eighty-five percent of all glaucoma. Other forms of glaucoma (such as angle closure glaucoma and secondary glaucoma) also involve decreased outflow through the canalicular pathway, but the increased resistance is from other causes such as mechanical blockage, inflammatory debris, cellular blockage, etc.

With the increased resistance, the aqueous fluid builds up because it cannot exit fast enough. As the fluid builds up, the intraocular pressure (IOP) within the eye increases. The increased IOP compresses the axons in the optic nerve and also may compromise the vascular supply to the optic nerve. The optic nerve carries vision from the eye to the brain. Some optic nerves seem more susceptible to IOP than others. While research is investigating ways to protect the nerve from an elevated pressure, the only therapeutic approach currently available in glaucoma is to reduce the intraocular pressure.

The clinical treatment of glaucoma is approached in a step-wise fashion. Medication often is the first treatment option. Administered either topically or orally, these medications work to either reduce aqueous production or to increase outflow. Currently available medications have many serious side effects including: congestive heart failure, respiratory distress, hypertension, depression, renal stones, aplastic anemia, sexual dysfunction, and death. Compliance with medication is a major problem, with estimates that over half of glaucoma patients do not follow their correct dosing schedules.

When medication fails to adequately reduce the pressure, laser trabeculoplasty often is performed. In laser trabeculoplasty, thermal energy from a laser is applied to a number of noncontiguous spots in the trabecular meshwork. It is believed that the laser energy stimulates the metabolism of the trabecular cells in some way, and changes the extracellular material in the trabecular meshwork. In approximately eighty percent of patients, aqueous outflow is enhanced and IOP decreases. However, the effect often is not long lasting and fifty percent of patients develop an elevated pressure within five years. The laser surgery is not usually repeatable with beneficial effect on pressure. In addition, laser trabeculoplasty is not an effective treatment for young primary open angle glaucoma patients, nor is it effective for angle closure glaucoma and many secondary glaucomas.

If laser trabeculoplasty does not reduce the pressure enough, then filtering surgery is generally performed. With filtering surgery, a hole is made in the sclera in the angle region. This hole allows the aqueous fluid to leave the eye through an alternate route.

The most commonly performed filtering procedure is a trabeculectomy. In a trabeculectomy, a posterior incision is made in the conjunctiva, the transparent tissue that covers the sclera. The conjunctiva is rolled forward, exposing the sclera at the limbus. A partial thickness scleral flap is made and dissected approximately one-half thickness into the cornea. The anterior chamber is entered beneath the scleral flap and a section of deep sclera and trabecular meshwork is excised. An iridectomy, a hole in the thus exposed iris, is made. The scleral flap is loosely sewn back into place. The conjunctival incision is tightly closed. Post-operatively, the aqueous fluid passes through the hole, beneath the scleral flap, and collects in an elevated space beneath the conjunctiva called a filtration bleb. The fluid then is either absorbed through blood vessels in the conjunctiva or traverses across the conjunctiva into the tear film.

Trabeculectomy is associated with many problems. Fibroblasts that are present in the episclera proliferate and migrate, and can scar down the scleral flap. Failure from scarring may occur, particularly in children, blacks, and young adults. Of eyes that have an initially successful trabeculectomy, many will fail from scarring within three to five years after surgery. To minimize fibrosis, surgeons now are applying antifibrotic agents such as mitomycin C (MMC) and 5-fluorouracil (5-FU) to the scleral flap at the time of surgery. The use of these agents has increased the success rate of trabeculectomy, but also has increased the prevalence of hypotony, and other serious complications. Hypotony is a problem that develops when aqueous flows out of the eye too fast, the eye pressure drops too low (usually less than 6.0 mmHg), and the structure of the eye collapses and vision decreases.

Trabeculectomy creates a pathway for aqueous fluid to escape to the surface of the eye and into the blood stream. At the same time, it creates a pathway for bacteria that normally live on the surface of the eye and eyelids to get into the eye. If this happens, an internal eye infection, called endophthalmitis, can occur. Endophthalmitis can occur anytime after trabeculectomy. The risk increases with the thin blebs that develop after the use of MMC and 5-FU. Another factor that contributes to infection is the placement of a bleb. Eyes that have trabeculectomy performed at the lower limbus have about five times the risk of eye infection than eyes that have a bleb superiorly protected by the upper lid. Therefore, trabeculectomy is usually performed superiorly under the eyelid, in either the nasal or temporal quadrant.

In addition to scarring, hypotony, and infection, there are other complications of trabeculectomy. The bleb can tear and lead to profound hypotony. The bleb can be irritating and can disrupt the normal tear film, leading to blurred vision and discomfort. Patients with blebs generally cannot wear contact lenses. The overwhelming majority of the complications from trabeculectomy stem from the fact that fluid is being diverted from inside the eye to the external surface of the eye, resulting in a bleb.

When trabeculectomy does not successfully lower the eye pressure, the next surgical step often is an aqueous shunt device. An aqueous diversion device of the prior art is a silicone tube that is attached at one end to a plastic (polypropylene or other synthetic material) plate. With an aqueous shunt device, an incision is made in the conjunctiva and Tenons, exposing the sclera. The plastic plate is sewn to the surface of the eye posteriorly, usually over the equator between two rectus muscles. A full thickness hole is made into the eye at the limbus, usually with a needle of approximately 22 gauge. The tube, which is connected to the plate, is inserted into the eye through this hole. The external portion of the tube is covered with either donor sclera or preserved pericardium. The conjunctival and Tenons incisions are closed tightly. Many problems exist with the current technology of aqueous shunt devices including scarring, failure, hypotony, corneal decompensation, tube erosion, suprachoroidal effusion and/or hemorrhage, and infection.

With prior art aqueous diversion devices, aqueous drains out of the eye through the silicone tube to the surface of the eye at the location of the plate or reservoir. Deeper orbital tissues then absorb the fluid. The outside end of the tube is protected from fibroblasts and scarring by the plastic plate. Many complications are associated with aqueous shunt devices. A thickened wall of scar tissue that develops around the plastic plate offers some resistance to outflow and in many eyes limits the reduction in eye pressure. In some eyes, hypotony develops because the flow through the tube is not restricted. Many physicians tie an absorbable suture around the tube and wait for the suture to dissolve post-operatively, at which time enough scar tissue has hopefully formed around the plate. Some devices contain a pressure-sensitive valve within the tube, although these valves may not function properly. The surgery involves operating in the posterior orbit and many patients develop an eye muscle imbalance and double vision. With prior art aqueous shunt devices, a pathway is created for bacteria to get into the eye and endophthalmitis can occur.

The prior art includes a number of such aqueous shunt devices, such as U.S. Pat. No. 4,936,825 (implanting in the cornea and limbal area a device partially embedded and partially extending anteriorly), U.S. Pat. No. 5,127,901 (directed to a transscleral shunt from the anterior chamber to the subconjunctival space), U.S. Pat. No. 5,180,362 (teaching a helical steel implant that is placed to provide drainage from the anterior chamber to the subconjunctival space), and U.S. Pat. No. 5,433,701 (apparatus includes an anterior portion configured for implantation through a scleral tunnel such that a leading edge thereof is within the anterior chamber).

In addition to the prior art aqueous shunt devices described above, other prior art devices for glaucoma surgery have used setons, or other porous, wick-like components to divert and convey excess aqueous from the anterior chamber to the exterior ocular surface. Examples include U.S. Pat. Nos. 4,634,418 and 4,787,885(teaching the surgical treatment of glaucoma using an implant that consists of a triangular seton (wick)), and U.S. Pat. No. 4,946,436, (teaching the use of a porous device to shunt anterior chamber to subscleral space). These patents do not teach placement in Schlemm's canal.

Some prior art references for glaucoma management have been directed at Schlemm's canal, but these have not involved the placement of long-term, indwelling shunts. U.S. Pat. No. 5,360,399 (teaches the temporary placement of a plastic or steel tube with preformed curvature in Schlemm's canal with injection of a viscous material through the tube to hydraulically expand and hydrodissect the trabecular meshwork). The tube is removed from the canal following injection. Because the tube is directed outwardly from the eye for injection access, the intersection of the outflow element with the preformed curved element within Schlemm's canal is at about a 90 degree angle relative to the plane of the curvature, and 180 degrees away from the anterior chamber. Therefore, at no time does any portion of the '399 device communicate with the anterior chamber. Furthermore, relative to that portion within Schlemm's canal, this tube has a larger diameter injection cuff element, which serves as an adapter for irrigation. Therefore, this device is not adapted for shunting aqueous between the anterior chamber and Schlemm's canal.

Most of the problems that have developed with current glaucoma treatment devices and procedures have occurred because aqueous fluid is drained from inside of the eye to the surface of the eye. A need exists, then, for a more physiologic system to enhance the drainage of aqueous fluid from the anterior chamber into Schlemm's canal. In the vast majority of glaucoma patients, the resistance problem lies between Schlemm's canal and the anterior chamber. The canal itself, the collecting channels, and the episcleral venous system all are intact. Enhancing aqueous flow directly into Schlemm's canal would minimize the scarring that usually occurs with external filtration procedure since the internal angle region is populated with a single line of nonproliferating trabecular cells. Enhancing aqueous flow directly into Schlemm's canal would minimize hypotony since the canal is part of the normal outflow system and is biologically engineered to handle the normal volume of aqueous humor. Enhancing aqueous flow directly into Schlemm's canal would eliminate complications such as endophthalmitis and leaks.

II. SUMMARY OF THE INVENTION

The present invention is a method and apparatus for treating glaucoma. The present invention treats glaucoma by lowering intraocular pressure in the eye so that the pressure level is tolerable for the optic nerve, which in turn, slows or stops the progression of damage and visual loss.

According to one aspect of the invention, a seton conducts aqueous directly from the anterior chamber to Schlemm's canal so that it can drain directly into the aqueous veins leading to the venous circulation. A seton for lowering intraocular pressure of an associated eye comprises a first tube adapted to be inserted into an associated anterior chamber of the eye; and, two wing tubes extending from the first tube. The two wing tubes are adapted to be inserted into Schlemm's canal. The two wing tubes and the first tube form a substantially continuous passageway, such that aqueous humor flows from the anterior chamber into Schlemm's canal through the substantially continuous passageway.

Another object of the present invention is to provide a seton, wherein the two wing tubes extend substantially perpendicular from the first tube.

Still another object of the present invention is to provide a seton, wherein the wing tubes have an outer diameter being no more than approximately 200 microns.

Yet another object of the present invention is to provide a seton, wherein the two wing tubes are tapered.

Further, another object of the present invention is to provide a seton, wherein the two wing tubes have an inner diameter ranging from substantially 80 microns to substantially 100 microns.

Still yet another object of the present invention is to provide a seton, wherein the first tube has an inner diameter ranging from substantially 280 microns to substantially 380 microns.

Another object of the present invention is to provide a seton, wherein the first tube has an outer diameter ranging from substantially 580 microns to substantially 680 microns.

Still another object of the present invention is to provide a seton, wherein the length of the first tube is approximately 1.5 cm.

Yet another object of the present invention is to provide a seton, wherein each of the two wing tubes has a length of approximately 1 cm.

Further, yet another object of the present invention is to provide a seton, wherein the first tube and the two wing tubes are composed of a biologically inert material.

Still another object of the present invention is to provide a seton, wherein the biologically inert material is silicone.

Still yet another object of the present invention is to provide a seton, further comprising at least one tab attached to one of the wing tubes, the tab having a fixation hole defined therein for securing the seton.

Yet another object of the present invention is to provide a seton, further comprising at least one port for clearing obstructions in the seton.

Further, another object of the present invention is to provide a seton, wherein the port may be defined in the first tube, in one of the two wing tubes, or in the intersection area formed by the first tube and the two wing tubes.

Another object of the present invention is to provide a seton, wherein the port is adapted for measuring intraocular eye pressure.

Still another object of the present invention is to provide a seton, further comprising pressure reading means for transmitting intraocular pressure readings to a pressure controller. In this embodiment the pressure controller is the pumping mechanism.

Yet another object of the present invention is to provide a method for draining aqueous humor from an associated anterior chamber of an eye, the method comprising the steps of providing an eye having a sclera and Schlemm's canal; providing a seton having a first tube and two wing tubes, the first tube adapted to be inserted into an associated anterior chamber of the eye, the two wing tubes extending from the first tube, the two wing tubes adapted to be inserted into Schlemm's canal, the two wing tubes and the first tube forming a substantially continuous passageway, whereby aqueous humor flows from the anterior chamber into Schlemm's canal through the substantially continuous passageway; dissecting the sclera so as to form a scleral flap and an intrascleral space, with or without the removal of scleral tissue; cutting Schlemm's canal to provide cut ends; inserting the first tube into the anterior chamber; inserting the two wing tubes into the cut ends of Schlemm's canal; closing the scleral flap, or otherwise covering the seton; and, draining aqueous humor from the anterior chamber to the Schlemm's canal.

Another object of the present invention is to provide a method for draining aqueous humor from an associated anterior chamber of an eye, further comprising the step of suturing the seton to the eye wall.

Still yet another object of the present invention is to provide a method for draining aqueous humor from an associated anterior chamber of an eye, further comprising the step of clearing obstructions disposed in the wing tubes through the port.

Further, another object of the present invention is to provide a method for draining aqueous humor from an associated anterior chamber of an eye, further comprising the step of monitoring aqueous outflow to assure proper placement of the wing tubes. It is to be understood that monitoring the flow has other purposes as well.

Still another object of the present invention is to provide a method for draining aqueous humor from an associated anterior chamber of an eye, further comprising the step of measuring intraocular pressure through the port.

According to another aspect of the present invention a device for directing aqueous humor from an anterior chamber to Schlemm's canal comprises a seton and a pumping mechanism operatively connected to the seton.

Another object of the present invention is to provide a device for directing aqueous humor from an anterior chamber to Schlemm's canal, wherein the pumping mechanism is adapted to draw aqueous humor from the anterior chamber through the first tube, into the wing tubes, and into Schlemm's canal.

Still another object of the present invention is to provide a device for directing aqueous humor from an anterior chamber to Schlemm's canal, wherein the first tube extends into the pumping mechanism and the two wing tubes extend outwardly from the pumping mechanism.

Further, yet another object of the present invention is to provide a device for directing aqueous humor from an anterior chamber to Schlemm's canal, wherein the pumping mechanism is implanted within an intrascleral dissection. The pumping mechanism can also be located on the surface of the sclera.

Yet another object of the present invention is to provide a device for directing aqueous humor from an anterior chamber to Schlemm's canal, wherein the pump has dimensions of approximately 2 mm long by approximately 2 mm wide by approximately 500 microns in thickness.

Another object of the present invention is to provide a device for directing aqueous humor from an anterior chamber to Schlemm's canal, wherein the pumping mechanism is implanted between associated rectus muscles.

Still yet another object of the present invention is to provide a device for directing aqueous humor from an anterior chamber to Schlemm's canal, wherein the pumping mechanism is implanted posterior to an associated limbus.

Further, another object of the present invention is to provide a device for directing aqueous humor from an anterior chamber to Schlemm's canal, wherein the pumping mechanism has length, width, and thickness dimensions of approximately 6 mm by approximately 10 mm by approximately 3 mm, respectively.

Another object of the present invention is to provide a device for directing aqueous humor from an anterior chamber to Schlemm's canal, wherein the pumping mechanism is adapted to operate on a demand basis, such that the required flow through the two wing tubes, to achieve the desired intraocular pressure, varies according to the diurnal fluctuation in aqueous production.

Still yet another object of the present invention is to provide a device for directing aqueous humor from an anterior chamber to Schlemm's canal, further comprising a feedback mechanism for monitoring work performed by the pumping mechanism to achieve the desired intraocular pressure.

Further yet, another object of the present invention is to provide a device for directing aqueous humor from an anterior chamber to Schlemm's canal, wherein the pumping mechanism is adapted to be adjusted without having to surgically dissect tissues to expose a large portion of the pumping mechanism.

According to another aspect of the present invention is to provide a method of draining aqueous humor from an anterior chamber to Schlemm's canal, the method comprising the steps of providing an eye having a sclera and Schlemm's canal; providing a seton and a pumping mechanism operatively connected to the seton, the seton having a first tube and two wing tubes, the first tube adapted to be inserted into an associated anterior chamber of the eye, the two wing tubes extending from the first tube, the two wing tubes adapted to be inserted into Schlemm's canal, the two wing tubes and the first tube forming a substantially continuous passageway, whereby aqueous humor flows from the anterior chamber into Schlemm's canal through the substantially continuous passageway; dissecting the sclera so as to form a scleral flap and an intrascleral space; cutting Schlemm's canal to provide cut ends; inserting the first tube into the anterior chamber; inserting the two wing tubes into the cut ends of Schlemm's canal; closing the scleral flap; activating the pump; and, draining aqueous humor from the anterior chamber to the Schlemm's canal.

In accordance with yet another aspect of the present invention, a device for directing associated aqueous humor from an associated anterior chamber to an associated Schlemm's canal includes a seton having a first tube adapted to be inserted into the anterior chamber and a second tube extending from the first tube, the second tube adapted to be inserted into the Schlemm's canal, the tubes forming a substantially continuous passageway, wherein the aqueous humor flows from the anterior chamber into the Schlemm's canal through the substantially continuous passageway, the second tube forming third and fourth tubes at an associated limbus, and a pump mechanism operatively connected to the seton.

Another aspect of the present invention is to provide a method of draining aqueous humor from an anterior chamber to Schlemm's canal, further comprising the step of implanting the pumping mechanism within the intrascleral dissection, or other ocular surface.

Still another aspect of the present invention is to provide a method of draining aqueous humor from an anterior chamber to Schlemm's canal, further comprising the step of implanting the pumping mechanism between rectus muscles.

Yet another aspect of the present invention is to provide a method of draining aqueous humor from an anterior chamber to Schlemm's canal, wherein the pumping mechanism is implanted posterior to a limbus.

Further, another aspect of the present invention is to provide a method of draining aqueous humor from an anterior chamber to Schlemm's canal, further comprising the steps of varying pumping mechanism output; and, achieving desired intraocular pressure according to diurnal fluctuation in aqueous humor production.

Another aspect of the present invention is to provide a method of draining aqueous humor from an anterior chamber to Schlemm's canal, further comprising the step of decreasing pumping mechanism output when a predetermined intraocular pressure is reached.

According to another aspect of the invention, the process relies on the known pressure gradient between the anterior chamber and the venous circulation to permit the desired level of aqueous runoff and intraocular pressure.

Still yet, according to another aspect of the invention, the device contains a control port within the portion of the device that is positioned in the scleral dissection.

III. BRIEF DESCRIPTION OF THE DRAWINGS

FIG. 10 is a front elevational view of the pumping mechanism;

FIG. 11 is a side view of FIG. 10 taken along line 11—11;

FIG. 12 is a bottom view of FIG. 10 taken along line 12—12; and,

IV. DETAILED DESCRIPTION OF THE INVENTION

Unlike viscocanalostomy, the implantation of the present invention does require entrance into the anterior chamber; however, it is under very controlled circumstances, and with little, if any, surgical manipulation inside the eye. By intubating the anterior chamber, any variability in the permeability of Descemet's membrane, a major concern with "nonpenetrating" operations such as viscocanalostomy, is eliminated. The present invention conducts aqueous directly into Schlemm's canal, avoiding obstruction by scar tissue that might form within an intrascleral dissection 62. The device contains no valves that can malfunction. Instead, it relies upon the known pressure gradient between the anterior chamber (9+ mmHg) and the venous circulation (7 mmHg) to permit the desired level of aqueous humor runoff and intraocular pressure.

Figure 1:
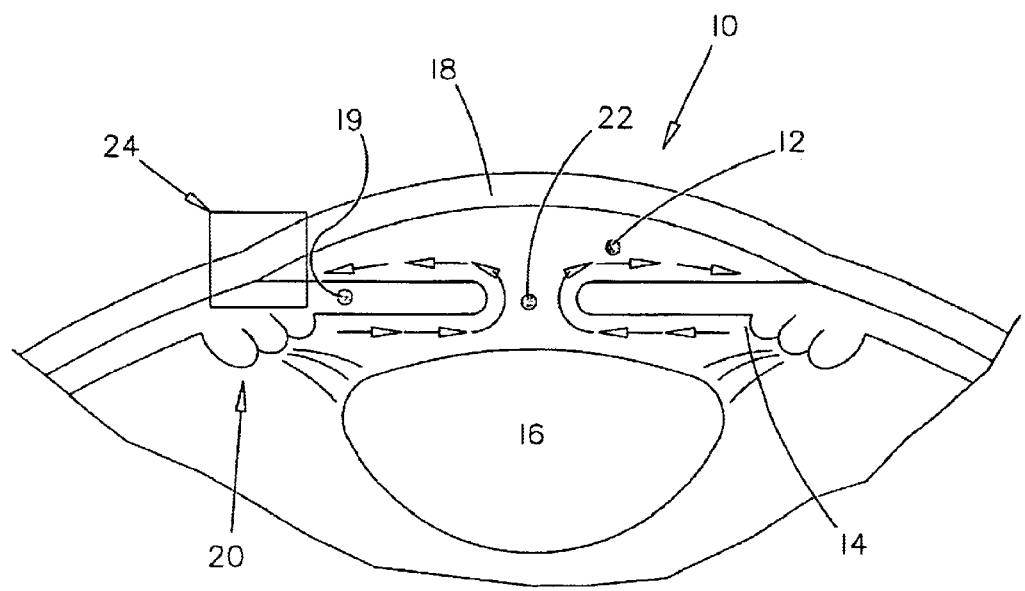
FIG. 1 is a partial cross-sectional view of an eye.
Figure 2:
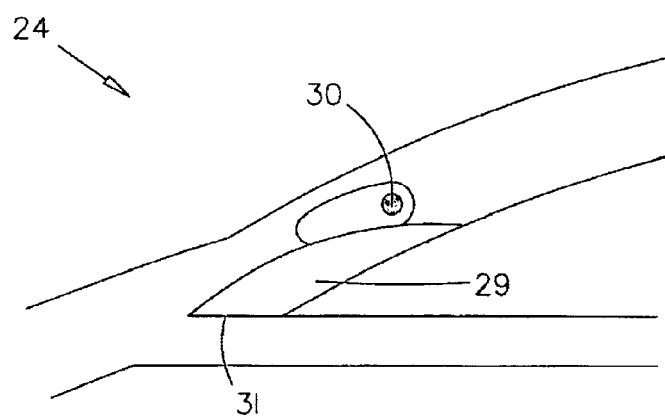
FIG. 2 is an enlarged view of the drainage angle.
Figure 3:
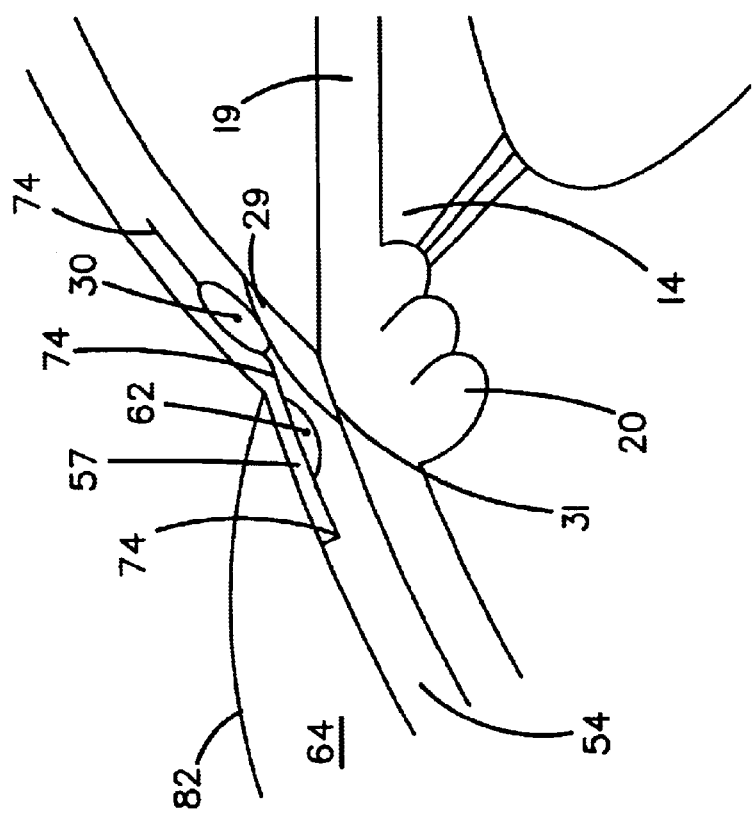
FIG. 3 is the drainage angle showing the incision.

Referring now to the drawings wherein the showings are for purposes of illustrating at least one preferred embodiment of the invention only and not for purposes of limiting the same, FIGS. 1–3 illustrate cross-sectional views of an eye 10. The anterior portion of the eye 10 is divided into two chambers: the anterior chamber 12 and the posterior chamber 14. Blood does not circulate in this part of the eye 10. Since blood does not circulate in this area, aqueous humor provides nourishment to lens 16 and cornea 18. The aqueous humor also maintains the intraocular pressure at normal levels. Ciliary processes 20, located in the posterior chamber 14 and behind peripheral iris 19, produce aqueous humor. The aqueous humor flows in front of the lens 16 and through pupil 22, into the anterior chamber 12, and out of the eye 10 through drainage angle 24. As shown in FIGS. 2 and 3, aqueous humor then passes into venous system (not shown) through trabecular meshwork 29 and into Schlemm's canal 30. A subconjunctival space 64 is shown, which is between the transparent tissue (the conjuctiva 82) that covers the sclera 54, and the sclera 54. Also shown in FIG. 3 is incision 74.

The outermost layers of the trabecular meshwork 29 constitute juxtacanalicular connective tissue 31. It is believed to be the site of greatest obstruction to aqueous humor outflow in cases of primary open angle glaucoma, the most common form of glaucoma in the Western World. From Schlemm's canal 30, the aqueous humor drains into the aqueous veins en route to the general venous circulation. This pathway accounts for over 80% of the drainage of aqueous humor from the eye 10. The remainder of the aqueous leaves the eye 10 through the uveoscleral pathway, which is independent of the trabecular meshwork 29.

Figure 4:
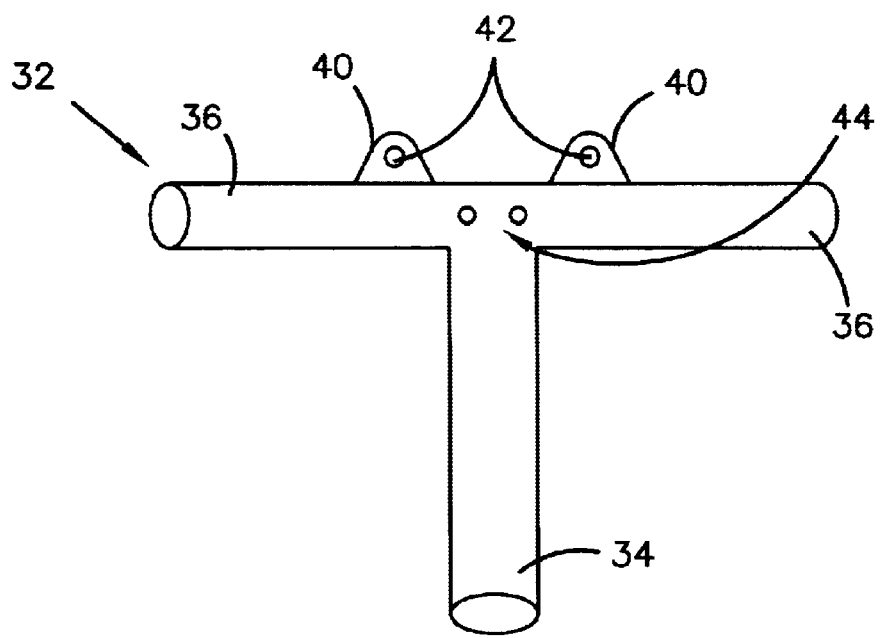
FIG. 4 is a top perspective view of the present invention.
Figure 5:
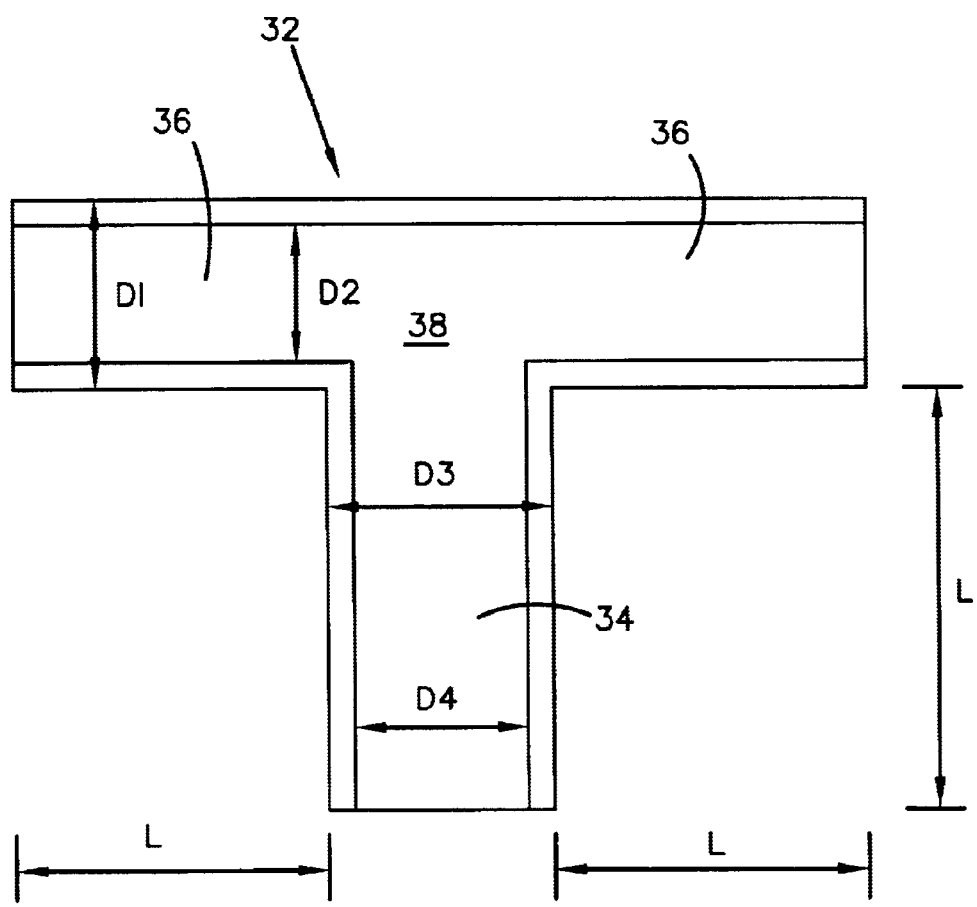
FIG. 5 is a cross-sectional view of the present invention.

As shown in FIGS. 4 and 5, the proposed invention is a seton 32 that conducts aqueous humor directly from the anterior chamber 12 to Schlemm's canal 30 so that it can drain directly into the aqueous veins leading to the venous circulation. This avoids the numerous complications of blebs as well as many of the other complications associated with filtration surgery. The seton 32 comprises a first tube 34 adapted to be inserted into the anterior chamber 12 of the eye 10. Two wing tubes 36 extend from the first tube 34. The two wing tubes 36 are adapted to be inserted into Schlemm's canal 30. The two wing tubes 36 and the first tube 34 form a substantially continuous passageway 38, such that aqueous humor flows directly from the anterior chamber 12 into Schlemm's canal 30 through the substantially continuous passageway 38.

Figure 9:
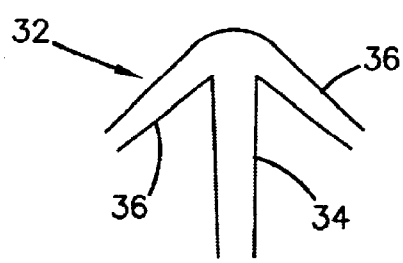
FIG. 9 is a front view of the present invention illustrating the wing tubes being tapered and angled relative to the first tube.

Turning to FIG. 9, the two wing tubes 36 may angularly extend from the first tube 34. As shown in FIGS. 4 and 5, the wing tubes 36 may extend substantially perpendicular from the first tube 34. Regardless of the angle between the two wing tubes 36 and the first tube 34, the two wing tubes 36 may be tapered to provide for easier insertion into Schlemm's canal 30, best seen in FIG. 9. It is also contemplated to be within the scope of the present invention that the first tube 34 and/or the two wing tubes 36 may be curved so that the surface conforms to the shape of the eye 10 and curvature of Schlemm's canal 30. For example, a radius of curvature for the eye 10 in these locations may be approximately twelve millimeters, and the radius of curvature for Schlemm's canal 30 may be approximately six millimeters. It is also to be understood that the wing tubes 36 could be impacted (i.e. tapered and/or slightly larger than Schlemm's canal 30), thereby creating a friction fit. The pumping mechanism 46 has a posterior surface, which is substantially concave in order to conform to the surface of the eye 10, when the pumping mechanism 46 is between the rectus muscles 50.

The seton 32 further comprises two tabs 40 attached to the wing tubes 36, as shown in FIG. 4. Each tab 40 has a fixation hole 42 defined therein for securing the seton 32 to the eye wall (i.e. sclera, cornea, and/or limbus). The fixation holes 42 serve as securing means for receiving sutures to secure the seton 32 in place. Although FIG. 4 illustrates the tabs 40 disposed along the two wing tubes 36, the tabs 40 may be positioned in any location chosen in accordance with sound engineering judgment. For example, FIG. 10 shows the tabs 40 disposed on a pumping mechanism 46.

Although not required, it is desirable for the seton 32 to comprise control ports 44. The ports 44 take the form of holes defined within the first tube 34 and/or the two wing tubes 36. In one embodiment, the ports 44 may be defined in the vicinity of the intersection of the first tube 34 and the two wing tubes 36. The ports 44 provide for clearing of the tubes 34, 36 with a microscopic obturator (not shown) if the tubes 34, 36 become obstructed with fibrin, blood, debris, and/or scar tissue. This would allow revision of failed operations with minimal dissection and risk. Further, the ports 44 could also be utilized for pressure measurements within Schlemm's canal 30 during surgery to guide the surgeon in placement of the seton 32. In it is to be understood that there are other reasons for measuring the pressure.

Figure 7:
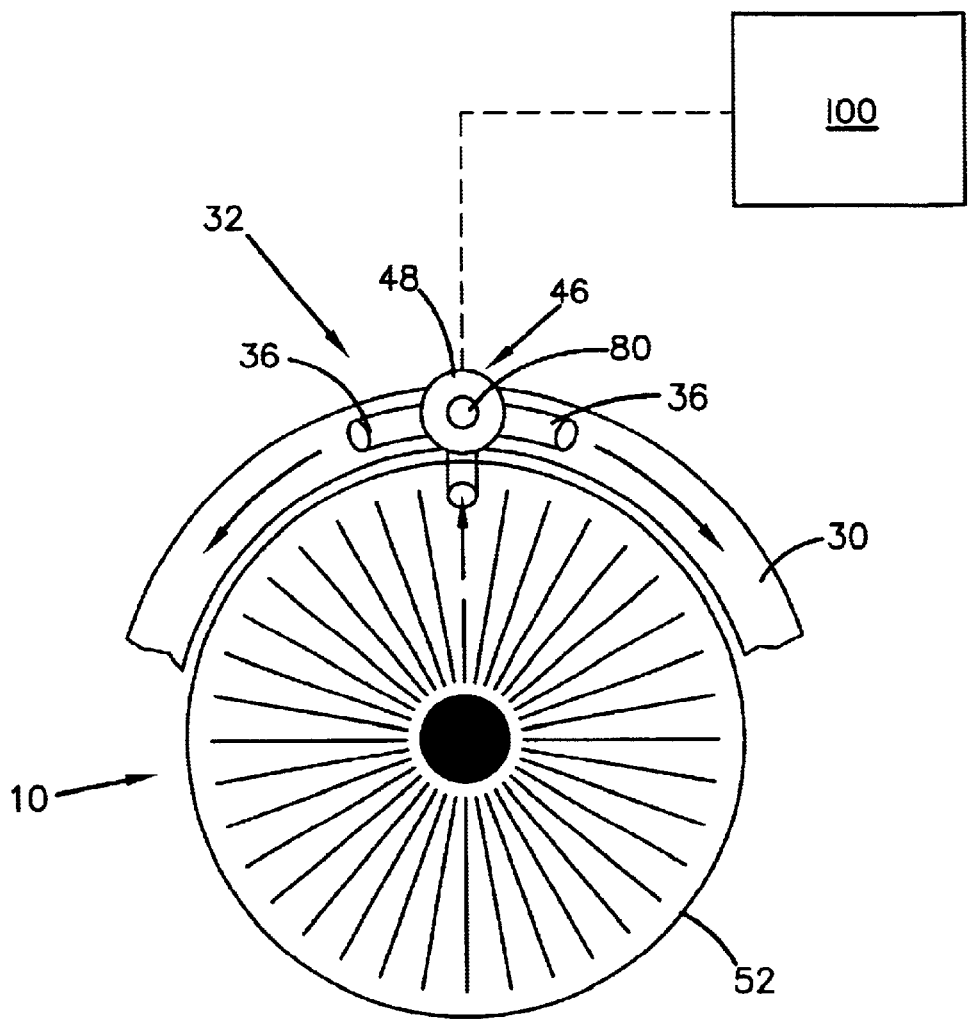
FIG. 7 is a front view of another embodiment of the present invention utilized in conjunction with a pump and a feedback control mechanism.
Figure 8:
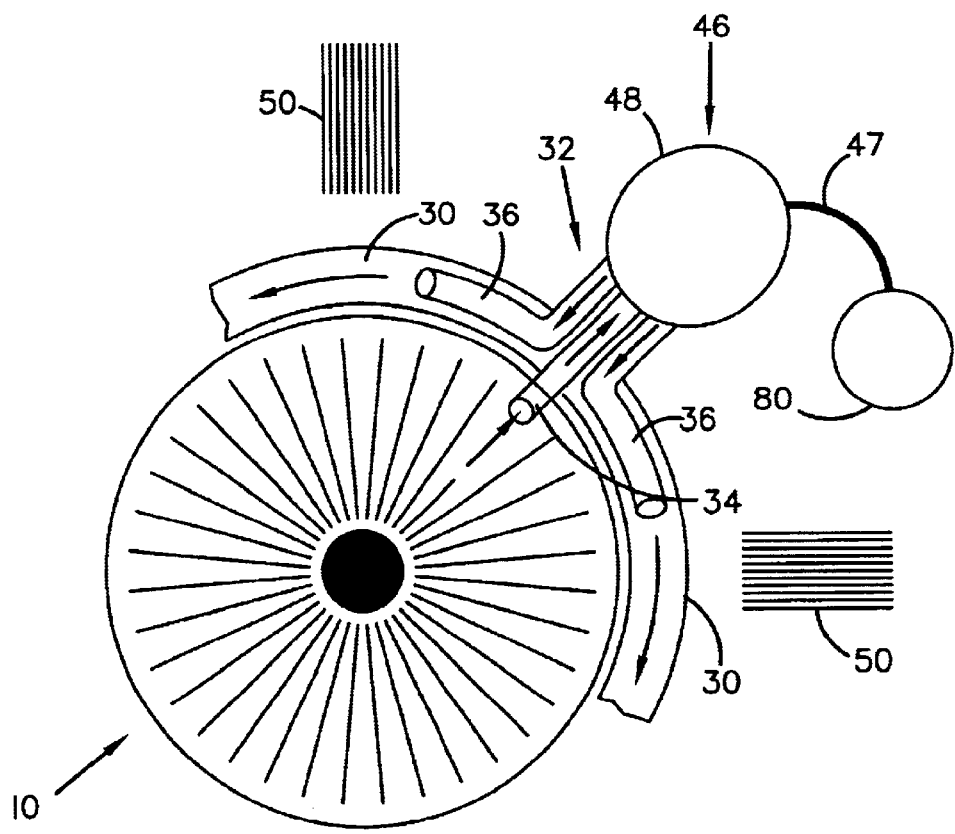
FIG. 8 is a front view of another embodiment of the present invention illustrating a different configuration with a pump.

In another embodiment of the invention, the first tube 34 acts as a passive conduit for aqueous humor to travel from the anterior chamber 12 to Schlemm's canal 30 (bypassing the trabecular meshwork 29), and may require help in the moving of the fluid in order to achieve the desired level of pressure in the eye 10. Eyes vary in their susceptibility to pressure-induced optic nerve damage and many eyes with glaucomatous damage require very low pressures to preserve what optic nerve tissue remains. In this embodiment, as shown in FIGS. 7 and 8, the pumping mechanism 46 is utilized in conjunction with the seton 32 in order to provide for better outflow of aqueous humor.

The pumping mechanism 46 is adapted to draw aqueous humor from the anterior chamber 12 and direct the aqueous humor into the two wing tubes 36 and into Schlemm's canal 30. The pumping mechanism 46 may take the form of a nanopump, which is generally a wafer 48 with tiny channels 72, which move polar solution by electric current, as shown in FIGS. 7, 8, and 10–12. Such pumps 48 are available through iMEDD, Inc., which has its principal place of business at 1224 Kinnear Road, Suite 130, Columbus, Ohio 43212. It is to be understood, however, that any pumping mechanisms that meets the size and flow requirements could be used. The pump 48 is encased in an insulative material 76, which protects against electrical surges. The material 76 also serves to protect the pump 48 from damage by force exerted by the eyelid during blinking or through dabbing or rubbing of the eye 10. The pump 48 can be made of any material chosen using sound engineering judgment. The insulative material 76, in this embodiment is silicone, but can be any biologically inert material. In one embodiment of the present invention, the nanopump channels 72 should have a minimum cross-sectional dimension between 2 and 100 nanometers and, preferably, between 10 and 30 nanometers. The channels 72 are shown as the spaces in the dotted line, shown as the wafer 48 in FIGS. 11 and 12.

With further reference to FIG. 12, the aqueous humor flows through first tube 34 into a first chamber 70. From the first chamber 70, the aqueous humor, via electric charge, passes through the wafer 48 through channels 72, and into a second chamber 78. From the chamber 78, the aqueous humor flows into wing tubes 36, and from there into Schlemm's canal 30.

It is also desirable for the nanopump 48 to have a voltage potential of approximately 0.5 to approximately 20 volts. Such a nanopump 48 is disclosed in a U.S. patent application, filed on Jun. 15, 2001, entitled Nanopump Apparatus and Method, co-invented by Derek Hansford, Ph.D., Assistant Professor of The Ohio State University and Rob J. Walczak, a scientist at iMEDD, Inc.

FIGS. 10–12 illustrate one embodiment of the pumping mechanism 46 in operative association with the seton 32. Turning to FIG. 10, the wafer 48 may range from approximately two to four millimeters in length and approximately two to four millimeters in width. Wires 47 extend from the wafer 48 to a power source 80, which may be batteries. The thickness of the working portion of the pumping mechanism 46 may be as thin as approximately three microns, and the total thickness of the wafer 48 may be as thin as approximately 200 microns.

Generally, the seton 32 and the pumping mechanism 46 may be implanted within the intrascleral dissection 62 laterally spaced from limbus 52, as in FIG. 7. In this embodiment, the power source 80 would be positioned between rectus muscles 50 (although it is to be understood that any location may be chosen for the power source 80, as long as chosen using sound engineering judgment. If wires 47 are utilized between the power source 80, the seton 32, and pumping mechanism 46, the wires 47 should be insulated. In this embodiment, power source 80 may be up to thirteen millimeters in diameter and up to three millimeters in thickness. In this embodiment, the dimensions of the pumping mechanism 46 should be fairly small. For example, length, width, and thickness dimensions may be about 2 mm by about 2 mm by approximately 500 microns, respectively. A posterior surface of the power source 80 may be substantially concave in order to conform to the surface of the eye 10.

In another embodiment of the invention, the pumping mechanism 46 and the power source 80 could be implanted in the same location as the glaucoma drainage seton 32, between the rectus muscles 50 approximately eight to ten millimeters posterior to the limbus 52, which is the same position where Ahmed and Molteno devices are located. In such a location, the pumping mechanism 46 and power source 80 could be much larger, such as approximately 6 mm by approximately 10 mm by approximately 3 mm in length, width, and thickness, respectively.

In another embodiment of this invention, the pumping mechanism 46 has a filter (not shown) to protect the pumping mechanism 46, as best seen in FIG. 8. The pumping mechanism 46 could also be treated with heparin, or other agents, to avoid clogging. In one embodiment, the operation of the pumping mechanism 46 would be utilized on a demand basis, such that the required flow through the first tube 34 to achieve the desired intraocular pressure would vary according to the diurnal fluctuation in aqueous production. A feedback mechanism 100 communicates with the pumping mechanism 46 to achieve the required flow rate, which results in the desired intraocular pressure. The feedback mechanism 100 may be integral with the pumping mechanism 46 or it may be a stand-alone unit. In order to avoid excessively low intraocular pressure, the pumping mechanism 46 may operate slower to decrease output of aqueous humor.

It is contemplated to be within the scope of the present invention that the pump speed be adjustable without having to surgically dissect tissues to expose a large portion of the pumping mechanism 46. Telemetry may also be utilized to provide intraocular eye pressure readings without the necessity of examining the patient.

The following dimensions are for illustration only and are not meant to serve as limitations. As best seen in FIG. 5, a cross-sectional view of the seton 32 is shown. The two wing tubes 36 have an outer diameter D1 and an inner diameter D2. The outer diameter D1 should be no more than approximately 200 microns, and more preferably no more than 180 microns. The inner diameter D2 may range from substantially 80 microns to substantially 100 microns. Like the wing tubes 36, the first tube 34 also has an outer diameter D3 and an inner diameter D4. The first tube 34 may have an inner diameter D4 ranging from approximately 280 microns to approximately 380 microns, and more preferably may be approximately 300 microns. The outer diameter D3 may range from approximately 580 microns to approximately 680 microns, and more preferably is approximately 630 microns. Each of the wing tubes 36 and the first tube 34 may have a length L1 and L2, respectively. The wing tube 36 length L1 may be approximately 1 cm, and the first tube 34 length L2 may be approximately 1.5 centimeters. The first tube 34 and the wing tubes 36 may be trimmed during a surgical procedure to ensure proper placement of the seton 32. As illustrated, the wing tubes 36 and the first tube 34 are shown to have equal lengths, but this is not required. The dimensions of the first tube 34 and the two wing tubes 36 may vary as long as the seton 32 may be effectively positioned in the eye 10 to properly drain aqueous humor into Schlemm's canal 30.

The seton 32 may be made of any material chosen in accordance with sound engineering judgment. Preferably, the material should be an inert material, such as silicone, but is not limited thereto.

Figure 6:
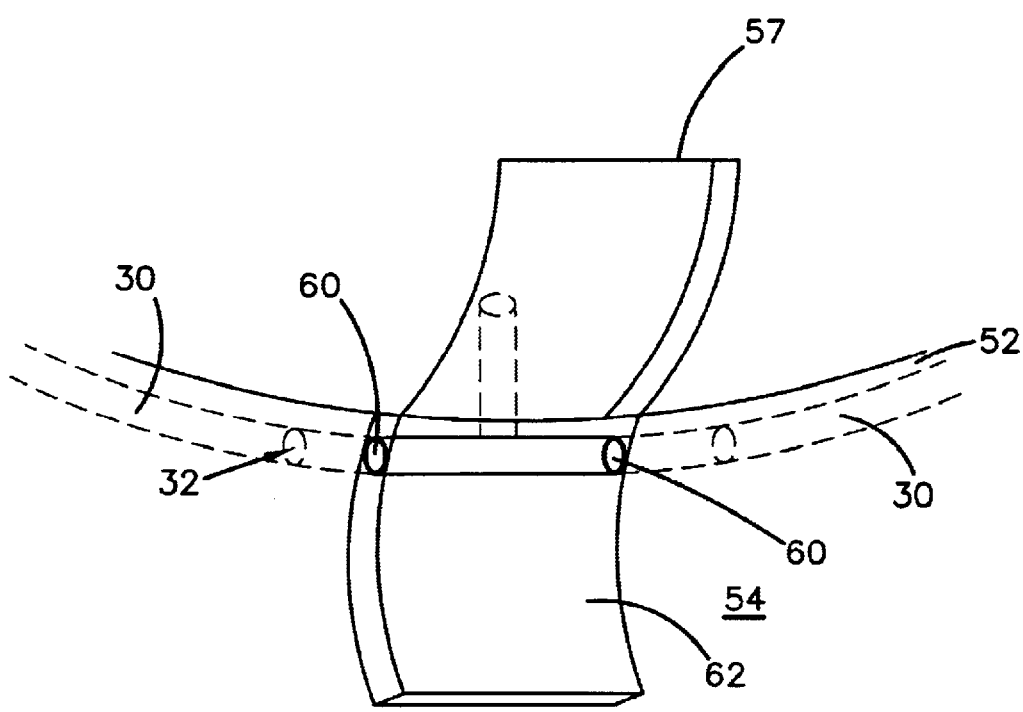
FIG. 6 is a perspective view of the present invention inserted into an intrascleral dissection.

In order to utilize the present invention, the seton 32 is provided, as previously described. The sclera 54 is dissected forming a scleral flap 57 and the intrascleral dissection 62, best seen in FIG. 6. The scleral flap 57 and the intrascleral dissection 62 are formed by the incision 74 as seen in FIG. 3. Next, Schlemm's canal 30 is cut to provide cut ends 60. The first tube 34 is inserted into the anterior chamber 12. The two wing tubes 36 are inserted into the cut ends 60 of Schlemm's canal 30. Next, the seton 32 is sutured into place through the holes 42 defined in the tabs 40. The scleral flap 57 is then closed. Aqueous humor can then be drained from the anterior chamber 12 directly into Schlemm's canal 30. Utilizing the control port 44 previously described, the method may further comprise the steps of clearing obstructions disposed in the wing tubes 36, monitoring aqueous humor outflow to assure proper placement of the wing tubes 36, and/or measuring intraocular pressure through the port 44 or through telemetry.

If the pumping mechanism 46 is provided, it may be activated to aid in the flow of aqueous humor. The pumping mechanism 46 may be implanted within the intrascleral dissection 62. Alternatively, the pumping mechanism 46 may be implanted between the rectus muscles 50 posterior to the limbus 52. The method described herein may further comprise the steps of varying pumping mechanism 46 output and achieving desired intraocular pressure according to diurnal fluctuation in aqueous humor production. When a predetermined intraocular pressure is reached, the pumping mechanism 46 output may be decreased. Another step to the foregoing method may include adjusting the pumping mechanism 46 output without having to surgically dissect tissues to expose a large portion of the pumping mechanism 46.

Figure 13:
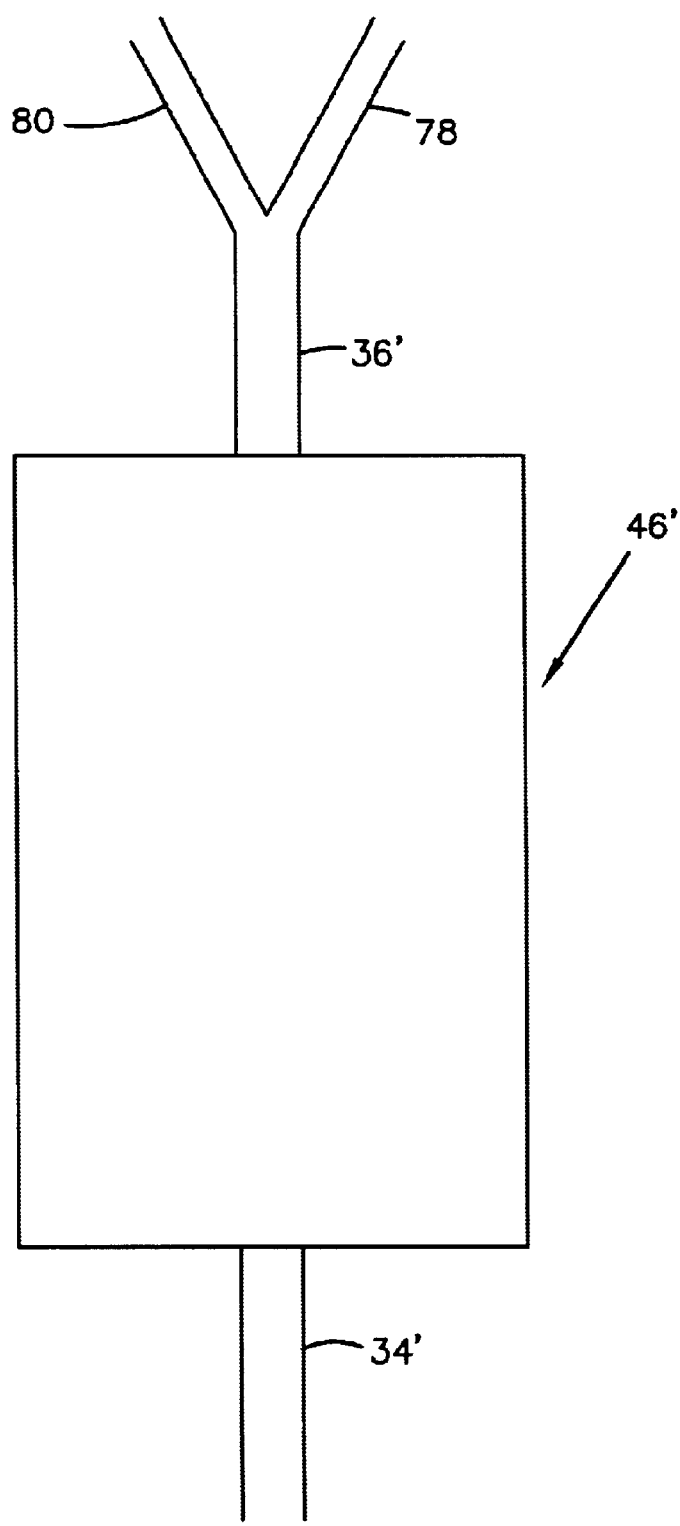
FIG. 13 is a front elevational view of another embodiment of the pumping mechanism.

With respect to FIG. 13, another embodiment of the invention is shown, wherein the pumping mechanism 46' only has one wing tube 36' that transfers the aqueous humor out of the pumping mechanism 46'. The tube 36' then splits at the limbus 52 into two tubes 78, 80, as shown in FIG. 13.

It is to be understood that the invention is not limited to the description in these embodiments of the tabs 40 and fixation holes 42. Any number of tabs 40 and holes 42 can be used, as well as any location of either, as long as the number and location are chosen using sound engineering judgment.

The invention has been described with reference to several embodiments. Obviously, modifications and alterations will occur to others upon a reading and understanding of the specification. It is intended by applicant to include all such modifications and alterations insofar as they come within the scope of the appended claims or the equivalents thereof.

What is claimed is:

1. A device for directing associated aqueous humor from an associated anterior chamber to an associated Schlemm's canal, the device comprising:
   a seton, comprising:
      a first tube adapted to be inserted into the anterior chamber; and,
      at least two wing tubes extending from the first tube, the two wing tubes adapted to be inserted into the Schlemm's canal, the two wing tubes and the first tube forming a substantially continuous passageway, wherein the aqueous humor flows from the anterior chamber into the Schlemm's canal through the substantially continuous passageway; and,
   a pump mechanism operatively connected to the seton.

2. The device of claim 1, wherein the two wing tubes extend substantially perpendicular from the first tube.

3. The device of claim 1, wherein the wing tubes have an outer diameter being no more than approximately 200 microns.

4. The device of claim 1, wherein the two wing tubes are tapered.

5. The device of claim 1, wherein the two wing tubes have an inner diameter ranging from approximately 80 microns to approximately 100 microns.

6. The device of claim 1, wherein the first tube has an inner diameter ranging from approximately 280 microns to approximately 380 microns.

7. The device of claim 1, wherein the first tube has an outer diameter ranging from approximately 580 microns to approximately 680 microns.

8. The device of claim 1, wherein the first tube has a length of the first tube is approximately 1.5 cm.

9. The device of claim 1, wherein each of the two wing tubes has a length of approximately 1 cm.

10. The device of claim 1, wherein the first tube and the two wing tubes are composed of a biologically inert material.

11. The device of claim 10, wherein the biologically inert material is silicone.

12. The device of claim 1, further comprising at least one tab attached to one of the wing tubes, the tab having securing means for securing the seton to an associated eye wall.

13. The device of claim 1, wherein the first tube and the two wing tubes form an intersection area, the intersection area comprising at least one port defined therein.

14. The device of claim 13, wherein the port is adapted to be used for clearing obstructions in the seton.

15. The device of claim 13, wherein the port is adapted to be used for measuring intraocular eye pressure.

16. The device of claim 1, wherein the pump mechanism is adapted to draw the aqueous humor from the anterior chamber through the first tube and into the Schlemm's canal.

17. The device of claim 1, wherein the first tube extends into the pump mechanism and the two wing tubes extend outwardly from the pump mechanism.

18. The device of claim 1, wherein the pump mechanism is implanted within an intrascleral dissection.

19. The device of claim 18, wherein the pump mechanism further comprises a power source operatively connected thereto.

20. The device of claim 19, wherein the power source is positioned in the intrascleral dissection.

21. The device of claim 19, wherein the power source is positioned between associated rectus muscles.

22. The device of claim 18, wherein the pump mechanism has length, width, and thickness dimensions of approximately 2 mm by approximately 2 mm by approximately 500 microns, respectively.

23. The device of claim 1, wherein the pump mechanism is implanted posterior to an associated limbus.

24. The device of claim 23, wherein the pump mechanism is implanted between associated rectus muscles.

25. The device of claim 24, wherein the pump mechanism further comprises a posterior surface, the posterior surface being concave.

26. The device of claim 24, wherein the pump mechanism further comprises a power source having a posterior surface, the posterior surface being concave.

27. The device of claim 23, wherein the pump mechanism has length, width, and thickness dimensions of approximately 6 mm, approximately 10 mm, and approximately 3 mm, respectively.

28. The device of claim 1, wherein the pump mechanism is adapted to operate on a demand basis, such that the required flow through the two wing tubes to achieve desired intraocular pressure varies according to diurnal fluctuation in aqueous production.

29. The device of claim 28, further comprising a feedback mechanism for monitoring work performed by the pump mechanism to achieve the desired intraocular pressure.

30. The device of claim 1, wherein the pump mechanism is adapted to be adjusted without having to surgically dissect tissues to expose a large portion of the pumping mechanism.

31. The device of claim 1, further comprising pressure reading means for transmitting intraocular pressure readings to a controller.

32. The device of claim 1, wherein the pump mechanism comprises a wafer.

33. The device of claim 32, wherein the wafer is surrounded by a microchip and an insulating protective layer.

34. The device of claim 1, wherein the pump mechanism is located on the surface of an associated eye.

35. A method of draining associated aqueous humor from an associated anterior chamber of an associated eye having an associated sclera, to an associated Schlemm's canal, the method comprising the steps of:

provide a seton and a pumping mechanism operatively connected to the seton, the seton having a first tube and at least two wing tubes, the first tube adapted to be inserted into the associated anterior chamber of the associated eye, the two wing tubes extending from the first tube, the two wing tubes adapted to be inserted into the associated Schlemm's canal, the two wing tubes and the first tube forming a substantially continuous passageway, such that the associated aqueous humor flows from the associated anterior chamber into the associated Schlemm's canal through the substantially continuous passageway;

dissecting the associated sclera so as to form a scleral flap and an intrascleral space;

cutting the associated Schlemm's canal to provide cut ends;

inserting the first tube into the associated anterior chamber;

inserting the two wing tubes into the cut ends of the associated Schlemm's canal;

covering the seton;

activating the pumping mechanism; and, draining the associated aqueous humor from the associated anterior chamber to the associated Schlemm's canal.

36. The method of claim 35, further comprising the step of:

implanting the pumping mechanism within the intrascleral dissection.

37. The method of claim 35, further comprising the step of:

implanting the pumping mechanism posterior to a limbus.

38. The method of claim 35, wherein the pumping mechanism is implanted posterior to a limbus between rectus muscles.

39. The method of claim 35, further comprising the steps of:

varying output from the pumping mechanism; and obtaining desired intraocular pressure according to diurnal fluctuation in the associated aqueous humor production.

40. The method of claim 35, further comprising the step of:

decreasing output from the pumping mechanism when a predetermined intraocular pressure is reached.

41. The method of claim 35, further comprising the step of:

adjusting the pump output without having to surgically dissect tissues to expose a large portion of the pumping mechanism.

42. The method of claim 35, further comprising the step of:

providing intraocular pressure readings through telemetry.

43. A device for directing associated aqueous humor from an associated anterior chamber to an associated Schlemm's canal, the device comprising:

a pump mechanism; and, a seton, comprising:

a first tube adapted to be inserted into the anterior chamber; and, a second tube extending from the pump mechanism, the second tube adapted to be inserted into the Schlemm's canal, the tubes forming a substantially continuous passageway, wherein the aqueous humor flows from the anterior chamber into the Schlemm's canal through the substantially continuous passageway, the second tube forming third and fourth tubes at an associated limbus.

* * * * *